United States Patent [19]

Lee et al.

[11] Patent Number: 5,053,513
[45] Date of Patent: Oct. 1, 1991

[54] METHOD OF REDUCING A CARBONYL CONTAINING ACRIDINE

[75] Inventors: Thomas B. K. Lee, Whitehouse Station; George E. Lee, Somerville; George S. K. Wong, Summit; Donna M. Borek, New Providence; Keith E. Goehring, Piscataway, all of N.J.

[73] Assignee: Hoechst-Roussel Pharmaceuticals Incorporated, Somerville, N.J.

[21] Appl. No.: 500,967

[22] Filed: Mar. 29, 1990

[51] Int. Cl.$^5$ .................................... C07D 219/10
[52] U.S. Cl. ........................................ 546/79; 546/93; 546/102
[58] Field of Search ........................... 546/79, 93, 102

[56] References Cited

U.S. PATENT DOCUMENTS

| | | | |
|---|---|---|---|
| 4,631,286 | 12/1986 | Shutske | 514/297 |
| 4,695,573 | 9/1987 | Shutske | 514/290 |
| 4,754,050 | 6/1988 | Shutske | 558/414 |
| 4,835,275 | 5/1989 | Shutske | 546/79 |
| 4,839,364 | 6/1989 | Shutske | 514/290 |
| 4,851,536 | 7/1989 | Skotnicki | 546/106 |
| 4,868,177 | 9/1989 | Shutske et al. | 514/228.2 |

OTHER PUBLICATIONS

Miles Hudlicky, "Reductions in Organic Chemistry", 1986, pp. 107–109 and table 18 in Appendix.
P. Rylander, Catalytic Hydrogenation in Organic Synthesis, 1979, pp. 48–51, 82–112 and 213–234.
M. Freifelder, Practical Catalytic Hydrogenation, 1971, pp. 59–69, pp. 282–313.
R. M. Acheson, ed., Acridines, 1st ed., 1956, pp. 271–276.
R. M. Acheson, ed., Acridines, 2nd ed., 1973, pp. 462–482.
N. S. Grigis et al., A New Synthesis of 4-Arylamino-2,3-polyethylenequinolines, Synthesis, 1985, pp. 547–548.
P. Finlander et al., Phosphorus Pentoxide in Organic Synthesis, Heterocycles, vol. 23, No. 6, 1985, pp. 1437–1444.
J. A. Moore et al., A Direct Syntheses of 4-Aminoquinolines, Tetrahedron Letters, No. 20, 1963, pp. 1277–1281.
J. Beilavsky, Analogues of 9-Amino-1,2,3,4-Tetrahydroacridine, Coll. Czech. Chem. Commun., vol. 42, 1977, pp. 2802–2808.
M. E. Konshin, Synthesis and Biological Activity of 9-alkyl-amino-1,2,3,4-tetrahydroacridines, 1971, pp. 10–12.
R. J. Chong et al., A Modified von Niementowski Quinoline Synthesis from Anthranilamides, Tetrahedron Letters, vol. 27, No. 44, 1986, pp. 5323–5326.
S. Singh et al., J. Hetero. Chem., vol. 5, 1968, pp. 737–739.

Primary Examiner—Mukund J. Shah
Assistant Examiner—Matthew V. Grumbling
Attorney, Agent, or Firm—Elliott Korsen

[57] ABSTRACT

A method of reducing a carbonyl containing acridine of the formula

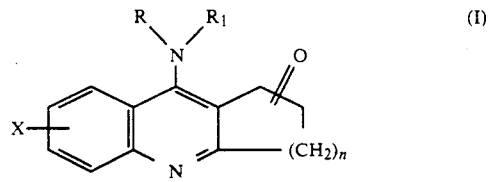

where n is 1, 2 or 3; X is hydrogen, loweralkyl, loweralkoxy, halogen, hydroxy, trifluoromethyl, or $NR_3R_4$ where $R_3$ and $R_4$ are independently hydrogen or loweralkyl; R is hydrogen or loweralkyl and $R_1$ is hydrogen, loweralkyl, diloweralkylaminoloweralkyl, arylloweralkyl, diarylloweralkyl, furylloweralkyl, thienylloweralkyl, oxygen-bridged arylloweralkyl, oxygen-bridged diarylloweralkyl, oxygen-bridged furylloweralkyl or oxygen-bridged thienylloweralkyl, is disclosed.

17 Claims, No Drawings

METHOD OF REDUCING A CARBONYL CONTAINING ACRIDINE

The present invention relates to a method of reducing a carbonyl containing acridine of the formula

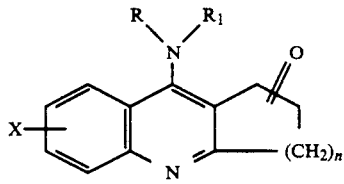

where n is 1, 2 or 3; X is hydrogen, loweralkyl, loweralkoxy, halogen, hydroxy, trifluoromethyl, or $NR_3R_4$ where $R_3$ and $R_4$ are independently hydrogen or loweralkyl; R is hydrogen or loweralkyl and $R_1$ is hydrogen, loweralkyl, diloweralkylaminoloweralkyl, arylloweralkyl, diarylloweralkyl, furylloweralkyl, thienylloweralkyl, oxygen-bridged arylloweralkyl, oxygen-bridged diarylloweralkyl, oxygen-bridged furylloweralkyl or oxygen-bridged thienylloweralkyl.

The reduction of these compounds is essential in the preparation of compounds which have been shown to be useful for enhancing memory. These include compounds of the formula

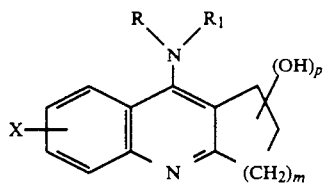

where p is 0 or 1; m is 1, 2 or 3; X is hydrogen, loweralkyl, loweralkoxy, halogen, hydroxy, trifluoromethyl, or $NR_3R_4$ where $R_3$ and $R_4$ are independently hydrogen or loweralkyl; R is hydrogen or loweralkyl; $R_1$ is hydrogen, loweralkyl, diloweralkylaminoloweralkyl, arylloweralkyl, diarylloweralkyl, thienylloweralkyl, oxygen-bridged arylloweralkyl, oxygen-bridged diarylloweralkyl, oxygen-bridged furylloweralkyl, oxygen-bridged furylloweralkyl, oxygen-bridged thienylloweralkyl; the optical antipodes thereof, or the pharmaceutically acceptable acid addition salts thereof.

Of particular interest is the reduction of compound Ia of the formula

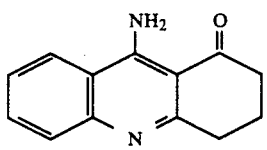

to (±)-9-amino-1,2,3,4-tetrahydroacridin-1-ol of the formula

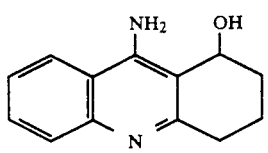

The carbonyl containing acridines and the alcohols prepared from their reduction are known as disclosed in U.S. Pat. Nos. 4,631,286, 4,695,573, 4,754,050, 4,835,275 and 4,839,364. The advantage of the subject invention for preparing the acridine derivatives is that it is less costly and provides high yields and high purity without undesirable side products. Accordingly, this invention aids in fulfilling the need for a process utilizing more economical, environmentally safer reagents which are more adaptable to large scale production. The target acridines are obtained in high yield and increased purity.

The substituents R, $R_1$, $R_3$, $R_4$, X, m, n and p are as defined above unless indicated otherwise.

The compounds are prepared according to the following sequence of reactions. Compound III of the formula

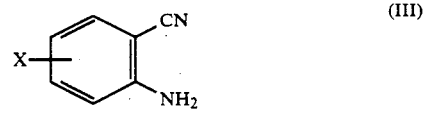

is reacted with Compound IV, a cyclic ketone of the formula

where p is 0 or 1 with the proviso that if p=1, the second carbonyl group is at the 2 or 3 position of the ring, to afford known intermediate, Compound V of the formula

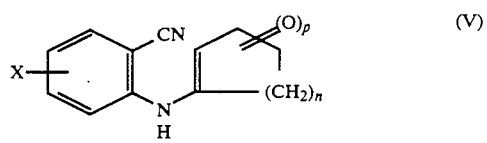

This reactions is typically conducted using a catalyst in a suitable solvent at a temperature of 80° to 180° C. (or to reflux) for 1 to 24 hours. A preferred temperature range is 110°-160° C. for 1 to 6 hours.

The catalyst is typically selected from p-toluenesulfonic acid monohydrate, methanesulfonic acid, sulfuric acid or the like; the preferred catalyst is p-toluenesulfonic acid monohydrate. The amount of catalyst necessary is typically in the range of 0.005 to 0.05 equivalents with 0.008-0.035 equivalents preferred. Solvents useful in the condensation include toluene, xylene, benzene or halogenated aromatic solvents such as chlorobenzene or dichlorobenzene. The preferred solvent is toluene.

The volume to weight (v/w) ratio of solvent to nitrile starting material is typically in the range of 1:3 to 1:10 with a preferred ratio of 1:4 to 1:6.

The reaction of Compound IV where n=2 and p=0 with Compound III affords the condensation product (Va) of the formula

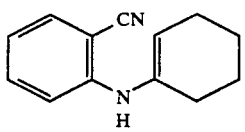

which is a useful intermediate in the preparation of Tacrine (9-amino-1,2,3,4-tetrahydroacridine hydrochloride hydrate).

Intermediate compound (V) where p is 1 is subsequently reacted with a catalyst in the presence of a basic inorganic salt in an amide solvent to afford Compound I.

This cyclization reaction typically utilizes a catalyst such as $FeCl_2 \cdot 4H_2O$, $FeCl_2$, $FeCl_3$, etc.; the preferred catalyst is $FeCl_2 \cdot 4H_2O$. There are significant advantages in using an iron catalyst rather than previously known copper or zinc catalysts in this cyclization step. Heavy metals such as copper and zinc are highly toxic and incompatible with microbial waste water treatment systems. If copper or zinc are released, they can cause serious environmental problems. Conversely, iron is essentially nontoxic and is even used in the treatment of waste water. The amount of catalyst employed is 5.0–13 mequiv.

Basic inorganic salts which are typically utilized include potassium and sodium carbonate and potassium and sodium bicarbonate. The preferred salts are potassium carbonate and potassium bicarbonate. The amount of salt employed is typically in the range of 5.0 to 30 mequiv.

The solvents which can be used in the cyclization include amide solvents such as dimethylformamide (DMF) or 1-methyl-2-pyrrolidinone; DMF is preferred. The v/w ratio of solvent to compound V is typically in the range of 3:1 to 5:1.

This cyclization is typically conducted at a temperature range of 130°–180° C. for 1 to 24 hours; preferred conditions include a range of 140°–160° C. for 1–8 hours.

Where compound Va is employed, under the typical conditions described above, Compound IIb (Tacrine) of the formula is prepared

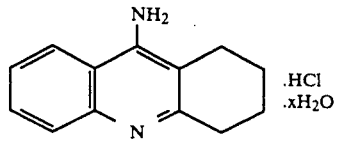

The target acridines are prepared by the reduction of either the free base or salt of compound Ia by two different methods. For large scale production, it is found that catalytic hydrogenation of the free base is the most practical method.

Compound I, in its free base form,

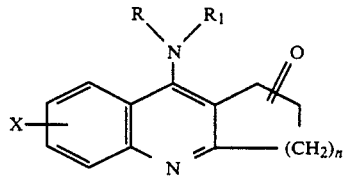

is reduced in a hydrogenation vessel charged under hydrogen pressure with a catalyst, alkali metal base and a solvent to afford Compound II.

Typically, a noble metal catalyst such as platinum is employed. The platinum can be in the form of the metal supported on an inert surface, e.g., on carbon or as the oxide or salt. The platinum content of the catalyst typically varies from about 1–10%, preferably in the range of 2–5%. The weight ratio of the noble metal contained in the catalyst to the starting ketone is generally 0.05 to 0.25%; the preferred weight ratio being 0.1 to 0.15%.

Alkali metal bases which can be employed in the reduction typically include sodium hydroxide or lithium hydroxide·$H_2O$ or the lower alkoxides of sodium or lithium. The preferred embodiment of the invention uses lithium hydroxide·$H_2O$ in a molar ratio of 0.1 to 0.5 equiv, preferably 0.2 equiv, with respect to the starting ketone.

Lower alkanol solvents with 2 to 8 carbons are typically employed. Preferred solvents are ethanol, 1-propanol, 2-propanol and 1-butanol. Most preferred of these solvents is 1-butanol. Aqueous mixtures of lower alkanol solvents can also be utilized. For instance, a small volume of water may be added to the solvent in order to increase the solubility of the alkali metal base. The amount of water added is generally in the range of 2 to 10%, preferably 5 to 7% w/w. The typical volume to weight ratio of solvent to ketone is in the range of 3:1 to 10:1, preferably 4:1 to 8:1.

The hydrogen pressure utilized is in the range of 50 to 1000 psi; typically in the range of 70 to 225 psi.

The reduction is typically conducted at an operating temperature range of 40°–100° C., for 4–20 hours; preferably in the range of 60°–80° C. for 6–10 hours.

The ratio of catalyst to base is typically 1:0.5 to 1:3, preferably 1:1 to 1:2.

It is critical in this process that the alkali metal base is present. We have shown that without the inclusion of the base, reduction occurs at a ratio which is much less than the ratio when the base is present. For example, it has been found that this ratio can be as much as 9 times greater utilizing lithium hydroxide monohydrate as the base (see example 5).

Compound I can be further reduced to its saturated form (Compound VI) of the formula

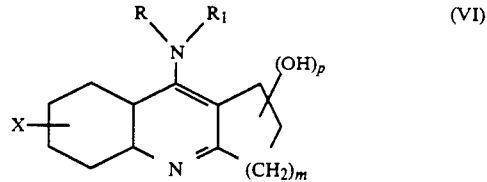

by elevating the temperature to a range of 120° to 150° C. for 1 to 4 hours.

Alternatively, the target alcohols can be prepared utilizing a safe, practical reduction method employing sodium borohydride.

The use of sodium borohydride provides a number of advantages over previously reported methods for the reduction of acridinones. First, a stabilized aqueous solution of sodium borohydride is much safer to use than other metal hydrides, e.g., lithium aluminum hydride, which are highly pyrophoric. Secondly, the use of an aqueous solvent is safer and more economical than the use of ethereal solvents such as ether, tetrahydrofuran or dioxane or amide solvents such as dimethylformamide or N-methyl-2-pyrrolidinone. Finally, the use of 5–25% v/v alcohol as a cosolvent effectively suppresses foaming, a severe problem which is always encountered when water or aqueous acid is used as a solvent.

In this alternative method, the acid addition salt of Compound I is reacted with sodium borohydride in a solvent mixture at a temperature of 20° to 60° C. for 1 to 5 hours, preferably the reaction takes place at a temperature range of 20° to 30° C. for 2 to 4 hours.

Typically, this reduction utilizes 0.8 to 1.3 equiv of sodium borohydride, optimally 0.9–1.0 equiv is used. The solvent mixture contains a lower alkanol and water. The lower alkanol is typically a $C_2$–$C_8$ alkanol; 2-propanol is preferred. The solvent system ranges from 5–23% of alkanol/water; preferred conditions utilize a 4 to 8% solution.

In this reduction, it is important to keep the pH of the reaction mixture properly adjusted. This is accomplished by the intermittent addition of acid during the reaction process.

The invention is described in greater detail in the following examples in which all parts, proportions, ratios and percentages are by weight unless otherwise indicated.

EXAMPLE 1

Synthesis of N-(3-oxocyclohexen-1-yl)-2-aminobenzonitrile

A mixture of aminobenzonitrile (50.0 g), 1,3-cyclohexanedione (52.14 g), and p-toluenesulfonic acid monohydrate (2.57 g) in toluene (250 ml) is refluxed for several hours with simultaneous removal of water by azeotropic distillation. The reaction mixture is cooled to room temperature, and then water (100 ml) is added. After stirring for 1–2 hours, the crude product is filtered and rinsed with toluene and water. The crude product is washed by slurrying with water (350 ml) at room temperature for 1–2 hours. The washed product, N-(3-oxocyclohexen-1-yl)-2-aminobenzonitrile, after filtration, rinsing with water and drying, is obtained in high yield.

EXAMPLE 2

Synthesis of 9-amino-3,4-dihydro-1(2H)-acridinone hydrochloride

A mixture of N-(3-oxocyclohexen-1-yl)-2-aminobenzonitrile (20 g), potassium bicarbonate (0.122 g) and ferrous chloride tetrahydrate (0.121 g) in dimethylforamide (DMF) (80 mL) is stirred at reflux for 2–6 hours.

After cooling the reaction mixture to 80°–85° C., 30% aqueous hydrochloric acid (12.1 mL) is added to acidify the mixture to a pH of 2.2–2.4 while maintaining a temperature of 80°–90° C. The crude product suspension is cooled and aged at 0°–5° C. for 1–2 hours. The crude product is filtered, rinsed with DMF (40 mL) and dried in vacuo to afford 22.7 g of 9-amino-3,4-dihydro-1(2H)-acridinone hydrochloride.

b. Purification of 9-amino-3,4-dihydro-1(2H)-acridinone hydrochloride

A solution of 9-amino-3,4-dihydro-1(2H)-acridinone hydrochloride (24.8 g) in water (175 mL) at 70°–80° C. is treated with charcoal (2–2.1 g), aged at 90°–100° C. for 0.5 hour, filtered and the filter cake is washed with hot water (24.8 mL). The combined filtrate at 85° C. is treated with 24% w/w aqueous sodium chloride (17 g) and aged at 0°–5° C. for 1 hour. Purified 9-amino-3,4-dihydro-1(2H)-acridinone hydrochloride (21.4 g) is obtained following filtration, water wash (24.8 mL) at 0°–5° C. and drying in vacuo.

c. Conversion of 9-amino-3,4-dihydro-1(2H)-acridinone hydrochloride to its free base A solution of 9-amino-3,4-dihydro-1(2H)-acridinone hydrochloride (100 g) in water (800 mL) at 80°–85° C. is basified by the addition of 50% sodium hydroxide (33.8 g) until the pH of the solution is greater than 11. The resultant slurry of product free base is aged at 60° C. for 0.5 hour, filtered and dried in vacuo to give 85.4 g of 9-amino-3,4-dihydro-1(2H)-acridinone.

EXAMPLE 3

Synthesis of (±)-9-amino-1,2,3,4-tetrahydroacridin-1-ol via catalytic hydrogenation Into a 300 ml autoclave under a nitrogen purge is charged 9-amino-3,4-dihydro-(1(2H)-acridinone (15.9 g), lithium hydroxide monohydrate (0.63 g), 3% Pt/C (1.26 g containing 58% water) and n-butanol (111 mL). The stirred mixture under a hydrogen atmosphere (125 psi), is heated to 70° C. After 10 hours the mixture contains 98.5% product by HPLC. The mixture is cooled to 25° C., vented, and purged with nitrogen. The product is dissolved as its acetate salt by addition of water (27.8 mL), acetic acid (6.5 g) and digestion at 25° C. for 30 minutes.

The dissolved product is separated from the Pt/C catalyst by filtration followed by a 80% aqueous n-butanol (15.9 mL) rinse. The combined filtrate is basified to a pH greater than 10.5 by addition of 50% sodium hydroxide (10.8 g) at 25°–30° C. and the resultant heterogeneous slurry is aged at 25° C. for 1 hour. The product, (±)-9-amino-1,2,3,4-tetrahydroacridin-1-ol, is isolated in 90.6% yield following filtration, 80% aqueous n-butanol (15.9 mL) wash, water (50 mL) wash, and drying in a vacuum oven.

The following table shows the effect on the yield of 9-amino-1,2,3,4-tetrahydroacridin-1-ol by varying some parameters of Example 3.

| Solvent | % Pt/C | Time | Hydrogen Pressure | Yield |
| --- | --- | --- | --- | --- |
| 2-Propanol | 3% | 8 hours | 150 psi | 94.1% |
| 2-Propanol | 2% | 14 hours | 70 psi | 94.5% |
| 1-Propanol | 5% | 10 hours | 70 psi | 94.2% |
| 2-Propanol | 5% | 10 hours | 70 psi | 81.5% |
| 1-Propanol* | 3% | 6 hours | 150 psi | 92.0% |
| 1-Propanol** | 3% | 6 hours | 150 psi | 91.7% |
| 1-Propanol*** | 3% | 6 hours | 150 psi | 94.7% |
| 1-Propanol**** | 3% | 8 hours | 150 psi | 89.8% |
| 1-Propanol***** | 3% | 6 hours | 150 psi | 83.0% |
| 2-Propanol€ | 3% | 6 hours | 380 psi | 97.7% |

*70° C.
**60° C.
***80° C.
****90° C.
*****100° C.
€50° C., 95% aqueous

EXAMPLE 4

Synthesis of (±)-9-amino-1,2,3,4-tetrahydroacridin-1ol via the sodium borohydride reduction method To a suspension of 9-amino-3,4-dihydro-1(2H)-acridinone hydrochloride (75 g), in a solvent mixture of 2-propanol (18.8 ml) and water (356 ml) is added portionwise, at room temperature, a solution of sodium borohydride (12.84 g) in 137.5 ml of 0.5% aqueous sodium hydroxide.

The pH of the reaction mixture is kept below 8.2 by the intermittent addition of 6N HCl. When the addition of the sodium borohydride solution has been completed, the pH of the reaction mixture is adjusted to 9.5-11 by the addition of 50% aqueous sodium hydroxide. The crude product, as the free base, is filtered and rinsed with water.

The wet crude product is suspended in a solvent mixture of 2-propanol and water at room temperature. Aqueous acetic acid (50-60%) is added to adjust the pH of the reaction mixture to 6-7. The mixture is stirred for several minutes until a homogenous solution is attained. The purified free base product, (±)-9-amino-1,2,3,4-tetrahydroacridin-1-ol can be obtained by rebasification with a 50% NaOH solution, filtration, rinsing with aqueous 2-propanol and water, and drying in a vacuum oven.

EXAMPLE 5

Catalytic hydrogenation of 9-amino-3,4-dihydro-1(2H)-acridinone to 9-amino-1,2,3,4-tetrahydroacridin-1-ol and 9-amino-1,2,3,4,5,6,7,8-octahydroacridin-1-ol without utilizing lithium hydroxide A 150 ml Parr hydrogenation vessel is charged with 9-amino-3,4-dihydro-1(2H)-acridinone (6.0 g), 3% Pt/C (with 65% $H_2O$) (0.86 g) and 1-butanol (42 ml). The mixture is pressurized and vented three times with nitrogen (70 psi) and three times with hydrogen (70 psi) at 23°-25° C. Following the final hydrogen purge, the flask is repressurized with hydrogen to 70 psi and heated to 70° C. with shaking. Samples were removed at 2, 4 and 12 hours for HPLC analyses. The results are given below in Table I.

TABLE 1

| Time | % Tetrahydro alcohol w/o LiOH | % Tetrahydro* alcohol w/LiOH | % Starting Ketone | % Octahydro Alcohol |
|---|---|---|---|---|
| 2 | 9.5% | 52.6% | 87.5% | 3.1% |
| 4 | 8.8% | 81.9% | 87.3% | 3.9% |
| 12 | 20.2% | 96.8% | 71.7% | 8.1% |

*similar experiment run using $LiOH.H_2O$ (0.2 equiv) as promoter.

EXAMPLE 6

Synthesis of N-(cyclohexen-1yl)-2-aminobenzonitrile

To a 300 ml, 3-neck round-bottom flask equipped with an overhead stirrer, Dean-Stark trap and thermometer was charged 13.3 g of 2-aminobenzonitrile, 133.5 ml of xylenes, 16.64 g of cyclohexanone and 0.905 g of p-toluenesulfonic acid monohydrate. The stirred solution was heated to reflux with simultaneous removal of water by azeotropic distillation for 9 hours. The mixture was then cooled to room temperature and poured into 150 ml of water. After stirring for 15 min., the phases were separated. The aqueous phase was extracted with 25 ml of xylenes and the combined organic phase was stirred with 100 ml of water for 10 minutes after the pH was adjusted to around 8 or 9 with 10% aqueous sodium hydroxide. The phases were separated; the organic phase was washed with 100 ml of water, dried over magnesium sulfate, filtered, and concentrated on a rotary evaporator to yield 20.87 g of an oil. The crude mixture was used in the next step without purification.

EXAMPLE 7

Synthesis of 9-Amino-1,2,3,4-tetrahydroacridine

To a 250 ml, 3-neck round-bottom flask equipped with an overhead stirrer, condenser and thermometer was charged 20.8 g of N-(cyclohexen-1-yl)-2-aminobenzonitrile, 90 ml of dimethylformamide, 2.26 g of ferrous chloride tetrahydrate and 1.13 g of potassium bicarbonate. The stirred mixture was refluxed for 2-4 hours, then allowed to cool. The reaction mixture was concentrated on a rotary evaporator to yield 21.72 g of an oil.

The oil was partitioned between toluene and 3N HCl; and the aqueous phase was basified to extract the product into dichloromethane. The organic phase was dried over potassium carbonate, filtered and concentrated on a rotary evaporator to yield 10.1 g of a solid. A second crop of 3.28 g was also isolated. The two solids were combined and purified via chromatography using silica gel to yield 8.3 g of 9-amino-1,2,3,4-tetrahydroacridine.

EXAMPLE 8

Synthesis of 9-benzylamino-1,2,3,4-tetrahydroacridin-1-ol via catalytic hydrogenation Into a 300 mL autoclave under a nitrogen purge is charged 9-benzylamino-3,4-dihydro-1(2H)-acridinone (22.7 g), lithium hydroxide monohydrate (0.63 g), 3% Pt/C (5.42 g containing 65% water) and n-propanol (159 mL). The stirred mixture (500 rpm), under a hydrogen atmosphere (400-1000 psi), is heated to 70° C. After 23 hours the mixture contains >99.5% product by HPLC. The mixture is cooled to 25° C., vented, and purged with nitrogen. The dissolved product is separated from the Pt/C catalyst by filtration followed by a n-propanol (22.7 mL) rinse. The combined filtrate is concentrated below 30° C. and the resultant heterogeneous slurry is aged at 5° C. for 1 hour. The product 9-benzylamino-1,2,3,4-tetrahydroacridin-1-ol, is isolated in 70% yield. (99.0% HPLC purity) following filtration, n-propanol wash, and drying in a vacuum oven.

We claim:

1. A method of reducing a carbonyl containing acridine derivative of the formula

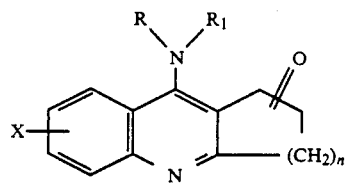

where n is 1,2 or 3 and X is hydrogen, loweralkyl, loweralkoxy, halogen, hydroxy, trifluoromethyl or $NR_3R_4$ where $R_3$ and $R_4$ are independently hydrogen or loweralkyl; R is hydrogen or loweralkyl; $R_1$ is hydrogen, loweralkyl, diloweralkylaminoloweralkyl, arylloweralkyl, diarylloweralkyl, furylloweralkyl, thienylloweralkyl, oxygen-bridged arylloweralkyl, oxygen-bridged diarylloweralkyl, oxygen-bridged furylloweralkyl or oxygen-bridged thienylloweralkyl which comprises reacting said carbonyl containing acridine with a noble metal catalyst under hydrogen pressure in the presence of an alkali metal base selected from lithium hydroxide and its hydrates in a suitable solvent.

2. The method of claim 1 wherein the alkali metal base is lithium hydroxide monohydrate.

3. The method of claim 1 wherein the carbonyl containing acridine is obtained by cyclizing a compound of the formula

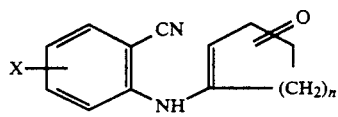

where n is 1, 2, or 3 and X is hydrogen, loweralkyl, loweralkoxy, halogen, hydroxy, trifluoromethyl, or $NR_3R_4$ where $R_3$ and $R_4$ are independently hydrogen or loweralkyl, in the presence of a metallic halide and a basic inorganic salt.

4. The method of claim 1 wherein the noble metal catalyst is platinum, platinum oxide or a platinum salt.

5. The method of claim 3 wherein the metallic halide is selected from the group consisting of ferrous chloride, ferric chloride and ferrous chloride tetrahydrate.

6. The method of claim 1 wherein the solvent is a lower alkanol solvent.

7. The method of claim 6 wherein the solvent is selected from the group consisting of ethanol, 1-propanol, 2-propanol and 1-butanol.

8. The method of claim 7 wherein the solvent is 1-butanol.

9. The method of claim 1 wherein 2 to 10% w/w water is added to the solvent.

10. The method of claim 1 wherein the catalyst is platinum, the alkali metal base is lithium hydroxide and the solvent is 1-butanol.

11. A method of reducing a compound of the formula

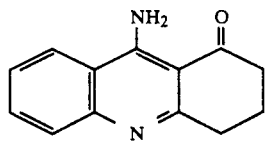

or a pharmaceutically acceptable acid addition salt thereof to a compound of the formula

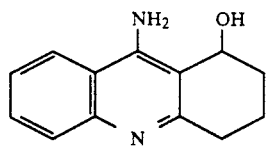

or a pharmaceutically acceptable acid addition salt thereof which comprises reacting the carbonyl containing compound with a noble metal catalyst in the presence of an alkali metal base selected from lithium hydroxide and its hydrates.

12. The method of claim 11 wherein the alkali metal base is lithium hydroxide monohydrate.

13. The method of claim 12 wherein the noble metal catalyst is platinum, platinum oxide or a platinum salt.

14. The method of claim 11 wherein the reduction product is a compound of the formula

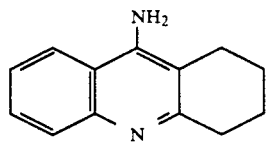

or the pharmaceutically acceptable acid addition salt thereof.

15. A method of preparing a compound of the formula

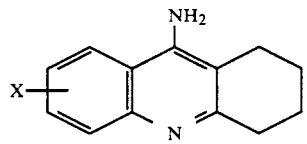

or the pharmaceutically acceptable acid addition salts thereof which comprises cyclizing a compound of the formula

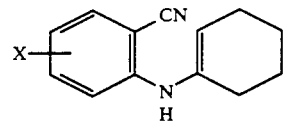

in the presence of iron halide or iron halide hydrate and a basic inorganic salt to obtain said compound.

16. The method of claim 15 wherein the metallic halide is ferrous chloride, ferric chloride or ferrous chloride tetrahydrate.

17. The method of claim 16 wherein the basic inorganic salt is potassium bicarbonate.

* * * * *